(12) United States Patent
Seifert et al.

(10) Patent No.: US 8,285,395 B2
(45) Date of Patent: Oct. 9, 2012

(54) CONDUCTIVE COUPLINGS, AND COMPONENTS THEREOF, FOR MEDICAL ELECTRICAL LEADS

(75) Inventors: Kevin R. Seifert, Forest Lake, MN (US); Gregory A. Boser, Richfield, MN (US)

(73) Assignee: Medtronic, Inc., Minneapolis, MN (US)

( * ) Notice: Subject to any disclaimer, the term of this patent is extended or adjusted under 35 U.S.C. 154(b) by 286 days.

(21) Appl. No.: 12/627,006

(22) Filed: Nov. 30, 2009

(65) Prior Publication Data

US 2010/0137954 A1    Jun. 3, 2010

Related U.S. Application Data

(60) Provisional application No. 61/118,602, filed on Nov. 29, 2008.

(51) Int. Cl.
*A61N 1/05* (2006.01)
*H01R 4/20* (2006.01)
(52) U.S. Cl. ........................ 607/116; 439/909
(58) Field of Classification Search .......... 607/115–117, 607/119, 122; 439/909
See application file for complete search history.

(56) References Cited

U.S. PATENT DOCUMENTS

| | | |
|---|---|---|
| 4,481,953 A | 11/1984 | Gold et al. |
| 4,603,705 A | 8/1986 | Speicher et al. |
| 5,105,826 A | 4/1992 | Smits et al. |
| 5,174,288 A | 12/1992 | Bardy et al. |
| 5,271,417 A | 12/1993 | Swanson et al. |
| 5,522,872 A | 6/1996 | Hoff |
| 5,676,694 A | 10/1997 | Boser et al. |
| 5,728,149 A | 3/1998 | Laske et al. |
| 5,928,277 A | 7/1999 | Laske et al. |
| 5,935,159 A | 8/1999 | Cross, Jr. et al. |
| 5,957,970 A | 9/1999 | Shoberg et al. |
| 6,016,436 A | 1/2000 | Bischoff et al. |
| 6,038,463 A | 3/2000 | Laske et al. |
| 6,038,472 A | 3/2000 | Williams et al. |
| 6,052,625 A | 4/2000 | Marshall |
| 6,061,595 A | 5/2000 | Safarevich |
| 6,181,971 B1 | 1/2001 | Doan |
| 6,256,542 B1 | 7/2001 | Marshall et al. |
| 6,259,954 B1 | 7/2001 | Conger et al. |
| 6,289,251 B1 | 9/2001 | Huepenbecker et al. |
| 6,615,695 B1 | 9/2003 | Hjelle et al. |
| 6,697,675 B1 | 2/2004 | Safarevich et al. |
| 6,704,604 B2 | 3/2004 | Soukup et al. |
| 6,801,809 B2 | 10/2004 | Laske et al. |
| 6,813,521 B2 | 11/2004 | Bischoff et al. |
| 6,920,361 B2 | 7/2005 | Williams |
| 7,031,777 B2 | 4/2006 | Hine et al. |

(Continued)

*Primary Examiner* — Carl H Layno
*Assistant Examiner* — Jessica Sarcione
(74) *Attorney, Agent, or Firm* — Reed A. Duthler (57) ABSTRACT

The present invention is configured to provide an offset weld and crimp in a coupling component that can be located entirely within a lumen of a lead body. This end is accomplished by providing an asymmetric coupling component is provided with a crimp recess, for example a groove or a bore extending along one side of the component and a thickened portion offset laterally from the groove or bore and having a welding surface displaced laterally from the groove or bore. While the embodiments illustrated herein are those employing a crimping groove, for purposes of understanding the invention it should be understood that a bore may be substituted. In preferred embodiments, the crimp recess is used to receive a stranded or cabled conductor within the lead body and the offset portion is used to attach to one or more filars of an electrode coil by welding thereto.

16 Claims, 4 Drawing Sheets

U.S. PATENT DOCUMENTS

| | | |
|---|---|---|
| 7,130,700 B2 | 10/2006 | Gardeski et al. |
| 7,277,762 B2 | 10/2007 | Belden et al. |
| 7,474,924 B2 | 1/2009 | Honeck et al. |
| 7,512,447 B2 | 3/2009 | Marshall et al. |
| 2004/0019372 A1* | 1/2004 | Cole .............................. 607/116 |
| 2004/0064173 A1* | 4/2004 | Hine et al. .................... 607/122 |
| 2005/0240252 A1 | 10/2005 | Boser et al. |
| 2007/0276458 A1 | 11/2007 | Boser |
| 2009/0254162 A1 | 10/2009 | Quinci et al. |

* cited by examiner

CONDUCTIVE COUPLINGS, AND COMPONENTS THEREOF, FOR MEDICAL ELECTRICAL LEADS

CROSS-REFERENCE TO RELATED APPLICATIONS

This application claims the benefit of U.S. Provisional Application No. 61/118,602, filed on Nov. 29, 2008. The disclosure of the above application is incorporated herein by reference.

TECHNICAL FIELD

The present disclosure pertains to medical devices, and more particularly to conductive couplings for medical electrical leads.

BACKGROUND

A medical electrical lead typically includes one or more elongate conductors, each of which electrically couples an electrode of the lead to a corresponding connector contact of the lead. A conductive coupling between a lead conductor and electrode should add a minimum of electrical resistance to the electrical circuit, which is formed by the electrode, conductor, and contact, and should have an adequate strength to maintain good contact under operational loading conditions.

Because medical electrical leads are typically constructed to have the lowest possible profile, without compromising functional integrity, reliability and durability, relatively low profile conductive couplings, which do not significantly increase a profile of the lead are also desired. Although some low profile conductive couplings have been previously disclosed, there is still a need for improved couplings which, in addition meeting the above criteria, provide flexibility in the manufacture of various configurations of medical electrical leads.

As lead bodies become smaller and the height of the connections between conductors and electrodes is reduced, it becomes increasing difficult to make low profile junctions that allow conductor coils to be welded to without damaging or significantly affecting the cable. For example, a radially symetrical crimp barrel or crimp sleeve located entirely within a lead lumen as described in U.S. patent application Ser. No. 11/549,284 filed Oct. 13, 2006, now abandoned, may only have a 3 mil wall due to height constraints. The thermal mass, wall thickness and available material to make an effective weld is negligible. Prior designs such as those disclosed in U.S. Pat. No. 5,676,694 issued to Boser et al and incorporated herein by reference in its entirety have provided an extension to the crimp sleeve which extends outward from the lead lumen to the exterior of the lead body, allowing the a weld to an associated electrode coil to be made spaced from the lead conductor. However, further reductions in lead profile are still desirable over leads fabricated using this connector mechanism.

SUMMARY OF THE INVENTION

The present invention is configured to provide an offset weld and crimp in a coupling component that can be located entirely within a lumen of a lead body. This end is accomplished by providing an asymmetric coupling component is provided with a crimp recess, for example a groove or a bore extending along one side of the component and a thickened portion offset laterally from the groove or bore and having a welding surface displaced laterally from the groove or bore. While the embodiments illustrated herein are those employing a crimping groove, for purposes of understanding the invention it should be understood that a bore may be substituted. In preferred embodiments, the crimp recess is used to receive a stranded or cabled conductor within the lead body and the offset portion is used to attach to one or more filars of an electrode coil by welding thereto.

The component displays a generally flattened configuration, with a thickness substantially less than its width as measured perpendicular to the crimp groove or bore. This configuration in turn allows the wall thickness and mass in the area of the weld to be significantly increased and moves the weld energy away form the cable while still maintaining a low profile. In order that the component does not add to the diameter of the lead body, it is preferably located in the lead so that the thickened offset portion extends from the groove or bore along either the longitudinal axis or around the circumference of the lead body. The component may also be provided with curved inner or outer surfaces extending across its width to assist in conforming to the typically cylindrical geometry of leads' internal lumens and surfaces.

The flat geometry and/or curved geometry of the coupling component allows for easy orientation of the component during the welding/assembly. The invention may also comprise an optional recessed region in the offset region of the sleeve. In addition, the electrode wires can be welded together to improve the ability of placing two or more electrode wires in a single recess region. This is particularly effective when attaching flat wire electrode coils to the sleeve. As a further embodiment/option, to aid the cable joining process the inner channel of the sleeve can incorporate an interlock that is engaged when clamping the sleeve on to the cable. This interlock can be useful when the coupling component is fabricated of a material that has spring back (e.g. Titanium).

In some embodiments, the conductor to which the coupling component is crimped is a cabled conductor extending parallel to the axis of the lead body and the groove or bore extends parallel to the axis of the lead body. In other embodiments, the conductor to which the coupling component is crimped is a coiled conductor having individual coils extending generally transverse to the axis of the lead body the groove or bore correspondingly extends generally transverse to the axis of the lead body. In embodiments in which employ a groove, as disclosed in more detail herein, the groove is defined is defined by first and second arms which define the groove therebetween.

The electrode preferentially takes the form of an electrode coil mounted around the outer circumference of the lead body and preferably includes a portion or component that component that extends through the outer insulation sidewall of the lead and into the interior lumen or space within the lead that encloses the lead conductor and the coupling component. The weld is thus located entirely within the outer diameter and preferably within the inner diameter of the lead body.

BRIEF DESCRIPTION OF THE DRAWINGS

The following drawings are illustrative of particular embodiments of the present disclosure and therefore do not limit the scope of the invention. The drawings are not to scale (unless so stated) and are intended for use in conjunction with the explanations in the following detailed description. Embodiments will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments. Examples of constructions, materials, dimensions, and manufacturing processes are provided for selected elements, and all other elements employ that which is known to those of skill in the field of the disclosure. Those skilled in the art will recognize that many of the examples provided have suitable alternatives that can be utilized.

Figure 1:
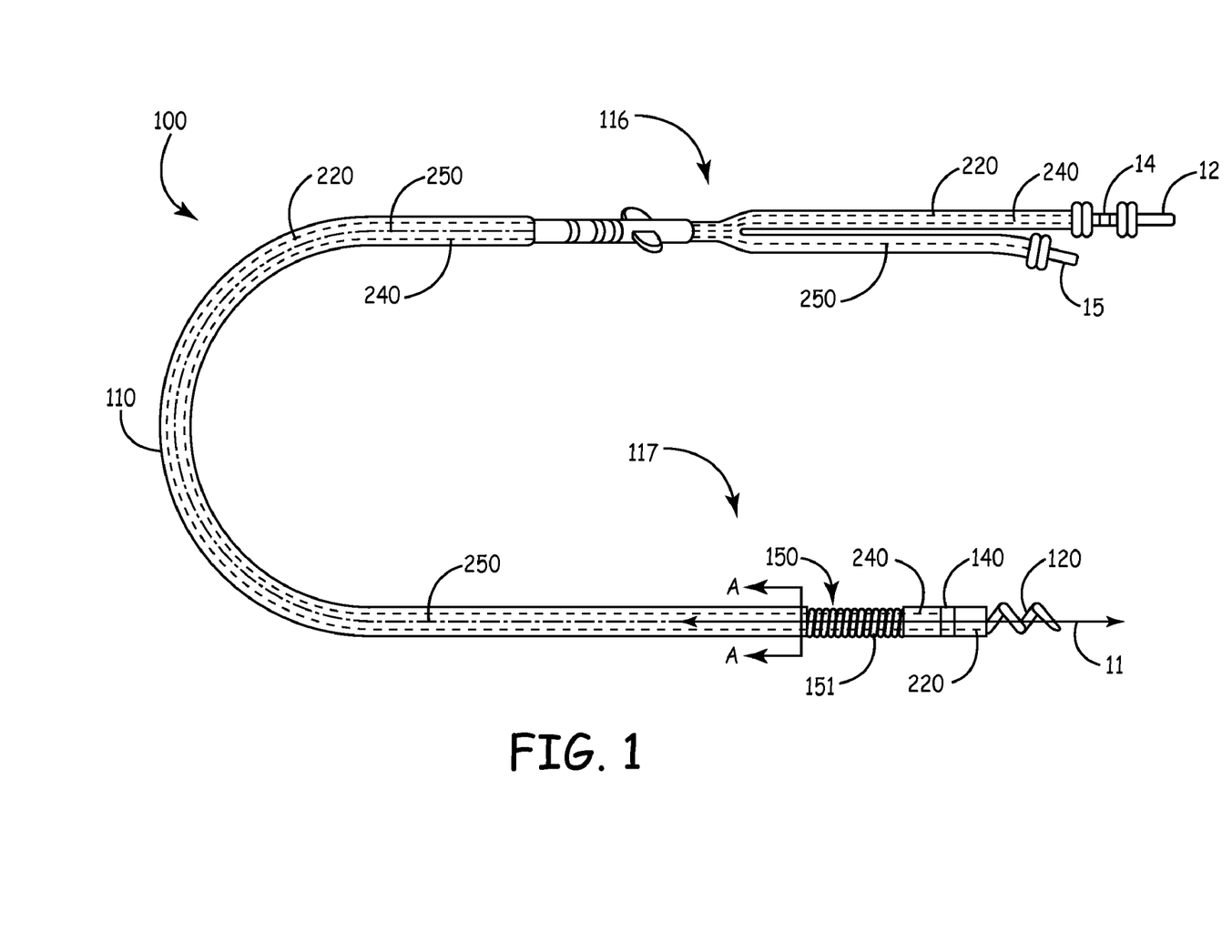
FIG. 1 is a plan view of an exemplary medical electrical lead that may include embodiments of the present invention.

FIG. 1 is a plan view of an exemplary medical electrical lead 100 that may include embodiments of the present invention. FIG. 1 illustrates lead 100 including an outer insulation sidewall 110 that extends between a proximal portion 116 and a distal portion 117; proximal portion 116 includes electrical contact surfaces 12, 14 and 15, which are shown mounted on connector legs of proximal portion 116; and distal portion 117 includes electrode surfaces 120, 140 and 151. Dashed lines in FIG. 1 schematically illustrate conductors 220, 240 and 250 which extend within outer insulation sidewall 110 to couple each of electrode surfaces 120, 140, 151 to a corresponding contact surface 12, 14, 15. Thus, lead 100 is a tripolar lead that may provide pacing and sensing, via electrode surfaces 120 and 140, and defibrillation, via electrode surface 151. According to some preferred embodiments, conductor 220 is formed as a coil to provide torque transfer between proximal portion 116 and distal portion and to electrically couple electrode surface 120 to contact surface 12, and conductors 240, 250 are each formed as a cable to electrically couple electrode surfaces 140, 151 to contact surfaces 14, 15, respectively. According to embodiments described herein, electrode surface 151 is a first portion of an electrode component 150, and a second portion of electrode component 150 extends within outer insulative sidewall 110 for coupling with conductor 250. It should be noted that either or both of the components including electrode surfaces 120 and 140 may also include portions which are coupled to the corresponding conductors 220, 240 in a manner similar to embodiments described herein.

Two exemplary lead configurations, or arrangements of conductors 220, 240, 250 will be described herein (a first in conjunction with FIGS. 2B-C and 3, and a second in conjunction with FIG. 5), but any suitable arrangement of conductors 220, 240, 250, within outer insulation sidewall 110, is within the scope of the present invention. Furthermore, it should be noted, that embodiments are not limited to inclusion in tripolar pacing and defibrillation leads, like lead 100, and lead 100 is only an exemplary type of lead used for the purpose of illustration.

Figure 2A:
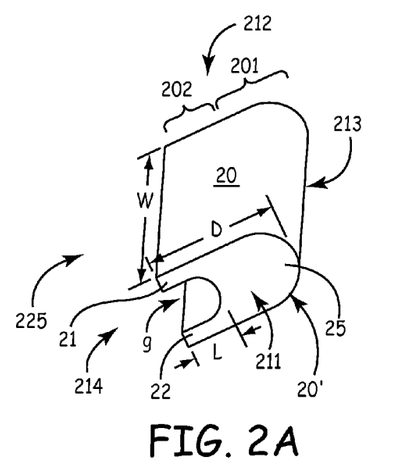
FIG. 2A is a perspective view of a coupling component, according to some embodiments.
Figure 2B:
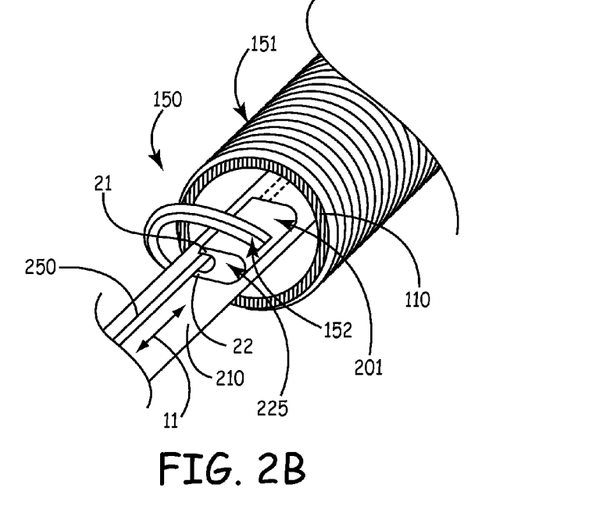
FIGS. 2B-C are each a perspective view of a portion of the lead shown in FIG. 1, wherein an outer insulation sidewall is cut away to show alternative conductive couplings, according to some alternate embodiments.
Figure 2C:
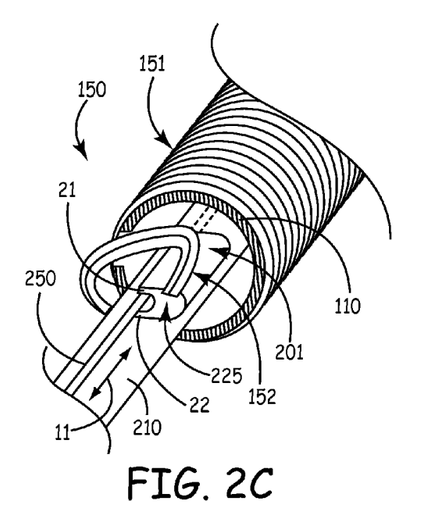

FIG. 2A is a perspective view of a coupling component 225, according to some embodiments, which may be incorporated into lead 100 to form the coupling between conductor 250 and the aforementioned second portion of electrode component 150. FIG. 2A illustrates coupling component 225, which is formed from a slug of conductive material, including a first side 211, a second side 212, which extends opposite first side 211, a third side, which extends between first and second sides 211, 212, and a fourth side 214, which also extends between first and second sides 211, 212, opposite third side 213. FIG. 2A further illustrates component 225 including a continuous bulk 25 of the slug of conductive material, which defines third side 213, and first and second arms 21, 22, each of which extend over a length L, from continuous bulk 25 to fourth side 214; each arm 21, 22 is shown having a width W, which is defined between first and second sides 211, 212. According to the illustrated embodiment, a space g between first and second arms 21, 22 of component 225 is intended to receive a length of an elongate conductor, for crimping between the arms, for example, conductor 250, as shown in FIGS. 2B-C. Although FIG. 2A shows length L being approximately the same for both arms 21, 22, it should be noted that, according to alternate embodiments, arms 21, 22 extend over different lengths; the differing lengths may facilitate an overlapping of arms 21, 22 when conductor is crimped therebetween, according to these alternate embodiments.

FIGS. 2B-C are each a perspective view of a portion of lead 100, generally coinciding with section line A-A of FIG. 1, wherein outer insulation sidewall 110 is cut away to show alternative couplings between electrode component 150 and conductor 250, via coupling component 225. FIGS. 2B-C illustrate conductor 250 extending between an inner insulation sidewall 210 and outer insulation sidewall 110, and coupling component 225 also located between sidewalls 210, 110 to receive a length of conductor 250, between arms 21, 22, for a crimp joint, and to receive a second portion 152 of electrode component 150 over a surface 20 thereof for a weld joint. Although not shown, it should be appreciated that conductor 220, which couples electrode surface 120 to contact surface 12 (FIG. 1), extends within inner insulation sidewall 210. Conductor 240 is also not shown, for the purpose of clarity in the illustration of the coupling; but, it should be appreciated that conductor 240 also extends between inner insulation sidewall 210 and outer insulation sidewall 110 to couple electrode surface 140 to contact surface 14. Dashed lines in FIGS. 2B-C illustrate an optional extension of conductor 250 beneath first portion 151 of electrode component 150, beyond the crimped junction with component 225, for example, to another junction with electrode component 150, at an opposite end thereof, according to some embodiments.

Figure 2D:
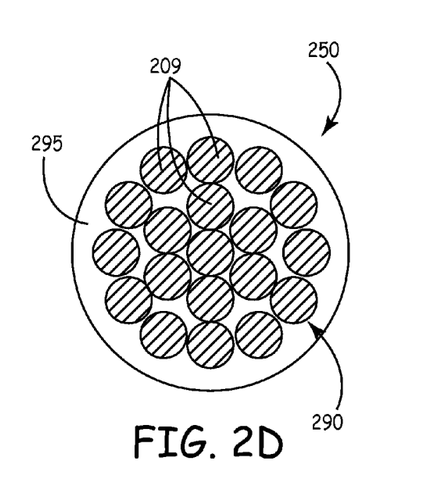
FIG. 2D is a cross-section view of an exemplary conductor.

According to the embodiments of FIGS. 2B-C, a length of conductor 250, about which arms 21, 22 are crimped, extends along width W of arms 21, 22 and, generally, in a direction of a longitudinal axis 11 of lead 100. Conductor 250 may include a 1×19 cable configured from a plurality of wire strands, for example, formed from MP35N alloy, which is known to those skilled in the art; a cross-section view of conductor 250 including such a cable is shown in FIG. 2D. Silver cored MP35N may also be employed. This present invention is even more important in this context as silver has lower melting point. The conductor wires may alternatively can be cable or solid conductors such as Ta or Ag cored MP35N. FIG. 2D illustrates cable 290 surrounded by an insulative jacket 295, for example, formed from a fluoropolymer, such as PTFE or ETFE; a portion of jacket 295 is removed from about cable 290, along the length of conductor 250 which is crimped between arms 21, 22, either prior to, or during the formation of the crimp. FIG. 2D further illustrates cable 290 made up of a plurality of wire strands 209, for example, each having a diameter between approximately 0.0005 inch and approximately 0.005 inch; strands 210 may be stranded with a pitch between approximately 0.3 inch and 0.6 inch. Another exemplary cable, that may form conductor 250, is known as a 7×7 cable, which includes seven cabled bundles of seven wire strands, and is described in commonly-assigned U.S. Pat. No. 5,760,341, which is hereby incorporated by reference.

According to some embodiments, width W of arms is at least approximately 0.02 inch, and, if a diameter of conductor 250 is approximately 0.006 inch (with insulative jacket 295 removed for the coupling), the space g between arms 21, 22 is approximately 0.008 inch and a length L over which arms 21, 22 extend is at least approximately 0.01 inch. A length of arms 21, 22 may be such that ends of arms do not overlap when the arms are crimped about the conductor, for example, by confronting crimp heads that indent arms 21, 22 on either side of conductor 250; but, according to alternate embodiments, for example, as will be describe below in conjunction with FIG. 3, a length of arms 21, 22 is such that one of arms overlaps the other when crimped.

With further reference to FIGS. 2A-C, a surface 20 of component 225, which faces outer insulation sidewall 110, is intended to receive an overlapping of second portion 152 of electrode component 150, for welding thereto, for example, via a solid state YAG type laser, known to those skilled in the art. FIG. 2A illustrates surface 20 of component 225 including a first part 201, which extends over continuous bulk 25, and a second part 202, which extends over first arm 21; a spot weld joint between second portion 152 of electrode component 150 and component 225 is preferably located along first part 201 of surface 20 so that a maximum thickness of conductive material, which is present in continuous bulk 25, as opposed to in arm 21, is available to maximize the weld pool for the joint. Locating the weld on first part 201 of surface 20 also helps to offset the weld joint from the crimp joint formed between arms 21, 22 and conductor 250, so that the formation of the two joints are less likely to compromise one another, while still allowing the entire coupling, between electrode component 150 and conductor 250, to reside beneath outer insulation sidewall 110. According to embodiments illustrated by FIG. 2B, second portion 152 of electrode component 150 extends, over first part 201 of surface 20 of component 225, in a direction transverse to the direction of longitudinal axis 11; while, according to embodiments illustrated by FIG. 2C, second portion 152 extends, over first part 201 of surface 20, in the general direction of longitudinal axis 11, similar to the extent of the crimped portion of conductor 250.

Suitable materials from which all, or at least second portion 152 of electrode component 150 may be formed include, without limitation, platinum-iridium alloy, tantalum, tantalum alloys, platinum-iridium clad tantalum and platinum-iridium clad tantalum alloys. Corresponding suitable materials from which component 225 may be formed, in order to accommodate laser welding between bulk 25 and second portion 152 of component 225, include, without limitation, platinum-iridium alloy, tantalum, tantalum alloys, titanium and titanium alloys. According to some preferred embodiments, if space g and length L of arms 21, 22 are dimensioned as described above, for conductor 250 as described above, and electrode component 150 is formed by a multi-filar coil, as illustrated, and each filar of the coil has a diameter between approximately 0.005 inch and approximately 0.01 inch, a thickness of bulk 25 (between surface 20 and an opposite surface 20') is between approximately 0.014 inch and approximately 0.02 inch, and an approximate area of first part 201 of surface 20 is the product of width W, which ranges from approximately 0.02 inch to approximately 0.06 inch, and a depth D, which ranges from approximately 0.01 inch to approximately 0.02 inch (FIG. 2A). Dimensions may correspondingly be reduced if smaller conductor cables are used. According to some alternate embodiments, electrode component 150 is a coil formed from a single filar, or wire, for example, having a diameter of between approximately 0.005 inch and approximately 0.01 inch. The single or multiple filars forming electrode component 150, according to some preferred embodiments, are formed from flattened, or ribbon, wire, rather than round wire; a cross-section of the flattened, or ribbon, wire may be defined by a width that is between approximately 0.005 inch and approximately 0.013 inch and a thickness, or height, that is between approximately 0.002 inch and approximately 0.005 inch.

Figures 3, 4A:
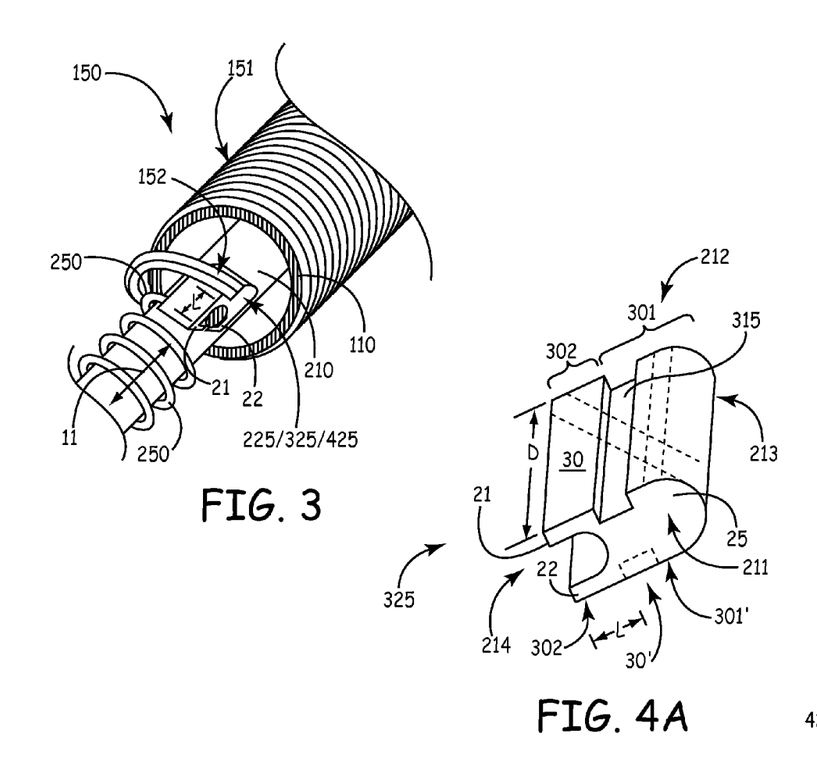
FIG. 3 is a perspective view of a portion of the lead shown in FIG. 1, wherein an outer insulation sidewall is cut away to show a conductive coupling, according to yet further embodiments.
FIGS. 4A-B are perspective views of coupling components, according to some alternate embodiments.

FIG. 3 is a perspective view of a portion of lead 100 (FIG. 1), generally coinciding with section line A-A of FIG. 1, wherein outer insulation sidewall 110 is cut away to show a conductive coupling, according to yet further embodiments. FIG. 3 illustrates an alternative orientation of both component 225 and the length of conductor 250, which is crimped between arms 21, 22 of component 225. According to the illustrated embodiment, conductor 250 is wound about inner insulation sidewall 210, and component 225 is oriented such that length L of arms 21, 22 extends generally in the direction of longitudinal axis 11 and the length of conductor 250, which is crimped between arms 21, 22, extends in the general direction of the winding of conductor 250, which is transverse to longitudinal axis 11. Although conductor 240 (FIG. 1) is not shown in FIG. 3, for the purpose of clarity in the illustration of the coupling, it should be appreciated that conductor 240 may also be wound about inner insulation sidewall 210, alongside conductor 250, and extends beneath electrode surface 151, being routed to a coupling with electrode surface 140 (FIG. 1). FIG. 3 further illustrates arm 21 overlapping arm 22 in the crimp about conductor 250, for example, having been formed by bending, either as an alternative to, or in addition to indenting, as described above.

FIG. 4A is a perspective view of a coupling component 325, according to some alternate embodiments, which may be employed, as a substitute for component 225, in the embodiments illustrated by FIGS. 2B-C and 3. It should be noted that suitable materials and dimensions for coupling component 325 may be the same as previously described for component 225. FIG. 4A illustrates coupling component 325 including the four sides 211, 212, 213, 214, the two arms 21, 22, and the continuous bulk 25, as previously described, such that component 325 has the same general form as component 225. FIG. 4A further illustrates a surface 30 of component 325 including a first portion 301, which extends over continuous bulk 25, a second portion 302, which extends over arm 21, and a groove 315, which is formed in first part 301 of surface 30 and extends orthogonally with respect to length L over which arms 21, 22 extend. According to the illustrated embodiment, groove 315 is located to receive one or both filars of second portion 152 of electrode component 150, so as to provide a positively identified position for second portion 152, for repeatability of welding, from one coupling to the next; and, according to some embodiments, groove 315 may be sized to be a friction fit about second portion 152, to further hold portion 152 in place for welding.

Dashed lines in FIG. 4A illustrate multiple alternate and/or additional locations and orientations for grooves, according to alternate embodiments of component 325. According to some alternate embodiments, component 325 includes an additional groove, which extends alongside groove 315, so that each filar of second portion 152 of electrode component 150 can extend in an independent corresponding groove. According to some further alternate embodiments, component 325 includes one or more grooves that extend at an angle less than 90 degrees with respect to length L over which arms 21, 22 extend. In order to make embodiments of component 325 less sensitive to orientation, and thereby increase manufacturing flexibility, a duplicate groove or set of grooves may be formed in a first part 301" of a surface 30" of component 325, which surface 30" is opposite surface 30.

Figure 4B:
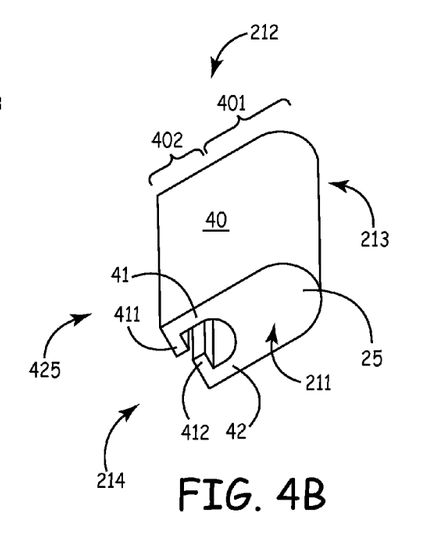
Figure 5:
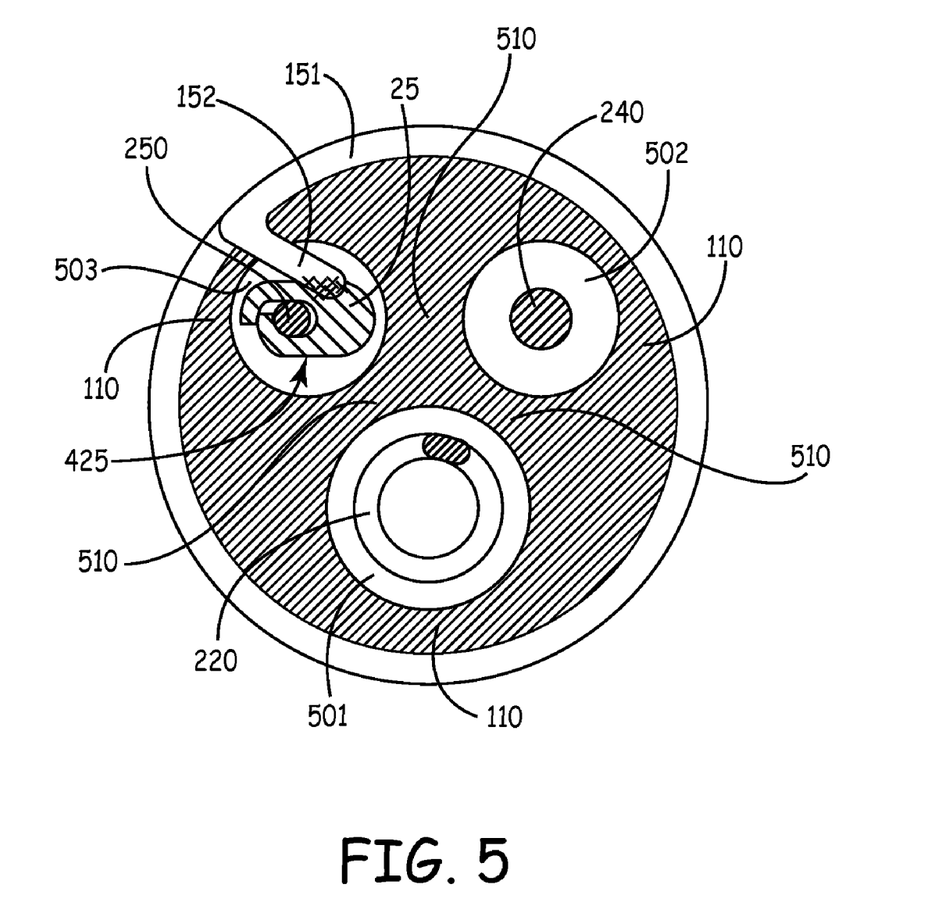
FIG. 5 is a cross-section through the lead of FIG. 1 showing a conductive coupling within an alternative insulative sidewall configuration, according to some alternate embodiments.

FIG. 4B is a perspective view of a coupling component 425, according to yet further alternate embodiments, which may also be employed, as a substitute for component 225, in the embodiments illustrated by FIGS. 2B-C and 3. It should be noted that suitable materials and dimensions for coupling component 425 may be the same as previously described for component 225. FIG. 4B illustrates coupling component 425 including the four sides 211, 212, 213, 214 and the continuous bulk 25, as previously described for component 225; in contrast to component 225, a first arm 41 of component 425 includes a terminal end 411 that extends toward a second arm 42 of component 425, and second arm 42 includes a terminal end 412 that extends toward first arm 41. FIG. 4B further illustrates each of terminal ends 411, 412 including an interlocking feature, so that arms 41, 42 mate together when crimped about a conductor, for example, conductor 250, as illustrated in FIG. 5. Like coupling components 225 and 325, component 425 includes continuous bulk 25 defining third side 213 and from which arms 41 and 42 extend; a surface 40 of coupling component includes a first part 401, which extends over continuous bulk 25, and a second part 402, which extends over first arm 41. According to the illustrated embodiment, and similar to the previously described embodiments, a spot weld joint between second portion 152 of electrode component 150 and component 425 is preferably located along first part 401 of surface 40 so that a maximum thickness of conductive material, which is present in continuous bulk 25, as opposed to in arm 41, is available to maximize the weld pool for the joint; such a joint is illustrated in FIG. 5.

FIG. 5 is a cross-section through medical electrical lead 100, at section line A-A of FIG. 1, showing a conductive coupling within an alternative insulative sidewall configuration, according to some alternate embodiments. FIG. 5 illustrates an inner insulative sidewall 510 of lead 100 being integral with outer insulative sidewall 110 in a multi-lumen tube configuration, wherein sidewalls 110 and 510 together form a first lumen 501, in which conductor 220 extends, a second lumen 502, in which conductor 240 extends, and a third lumen 503, in which conductor 250 extends. FIG. 5 further illustrates, a conductive coupling between conductor 250 and electrode component 150 located in third lumen 503; the illustrated coupling is formed by interlocking arms 41, 42 of coupling component 425 crimped about a length of conductor 250 and by a weld joint formed between second portion 152 of electrode component 150 and continuous bulk 25 of coupling component 425.

In the foregoing detailed description, specific embodiments have been described. However, it may be appreciated that various modifications and changes can be made without departing from the scope of the invention as set forth in the appended claims.

We claim:

1. A medical electrical lead, comprising:
   an outer insulation sidewall extending along a lead axis and having an outer diameter;
   a coupling component formed from a slug of conductive material and being entirely contained within the outer diameter of the outer insulation sidewall, the coupling component including,
     a crimping recess extending along one side of the component, and
     a thickened portion offset laterally from the crimping recess and extending therefrom in a direction parallel to the lead axis, the thickened portion having a welding surface displaced laterally along a longitudinal axis or around a circumference of the lead and entirely within the outer insulation sidewall, and
   an electrode component mounted around the outer insulation sidewall, the electrode component including a first portion defining an electrode surface and a second portion extending from the first portion to within the outer diameter of the outer insulation sidewall and over the welding surface of the coupling component and being welded thereto.

2. The lead of claim 1, wherein the crimping recess comprises a crimp groove located between first and second arms extending laterally from the thickened portion.

3. The lead of claim 2, wherein a length of the conductor, about which the arms of the coupling component are crimped, extends in a direction parallel to the lead axis.

4. The lead of claim 3, wherein the thickened portion of the coupling component extends from the arms in a direction transverse to the lead axis.

5. The lead of claim 2, wherein a length of the conductor, about which the arms of the coupling component are crimped, extends in a direction transverse to the lead axis.

6. The lead of claim 5, wherein the second portion of the electrode component extends in a direction transverse to the lead axis.

7. The lead of claim 5, wherein the thickened portion of the coupling component extends from the arms in direction parallel to the lead axis.

8. The lead of claim 1, wherein the second portion of the electrode component extends in a direction parallel to the lead axis.

9. The lead of claim 1, wherein the electrode component comprises a coiled wire.

10. The lead of claim 9, wherein the wire has a flattened cross-section.

11. The lead of claim 1 wherein the thickened portion comprises at least one groove therein in which the second portion of the electrode is located.

12. The component of claim 11, wherein the at least one groove extends at an angle less than 90 degrees with respect to the crimping recess.

13. The component of claim 11, wherein the at least one groove comprises a plurality of grooves.

14. A medical electrical lead, comprising:
   an outer insulation sidewall extending along a lead axis and having an outer diameter;
   a coupling component formed from a slug of conductive material and being entirely contained within the outer diameter of the outer insulation sidewall, the coupling component including a crimping recess extending along one side of the component and a thickened portion offset laterally from the recess and having a welding surface displaced laterally from the recess, an electrode component mounted around the outer insulation sidewall, the electrode component including a first portion defining an electrode surface and a second portion extending from the first portion to within the outer diameter of the outer insulation sidewall and over the welding surface of the coupling component and being welded thereto, wherein the crimp recess comprises a crimp groove located between first and second arms extending laterally from the thickened portion and wherein each of the first and second arms of the coupling component includes a terminal end; and the terminal ends interlock with one another.

15. A medical electrical lead, comprising:

an outer insulation sidewall extending along a lead axis and having an outer diameter;

a coupling component formed from a slug of conductive material and being entirely contained within the outer diameter of the outer insulation sidewall, the coupling component including a crimping recess extending along one side of the component and a thickened portion offset laterally from the recess and having a welding surface displaced laterally from the crimping recess, an electrode component mounted around the outer insulation sidewall, the electrode component including a first portion defining an electrode surface and a second portion extending from the first portion to within the outer diameter of the outer insulation sidewall and over the welding surface of the coupling component and being welded thereto, wherein the crimping recess comprises a crimp groove located between first and second arms extending laterally from the thickened portion and wherein the length of the conductor, about which the arms of the coupling component are crimped, extends in a direction transverse to the lead axis and wherein the thickened portion of the coupling component extends from the arms in direction parallel to the lead axis.

16. A medical electrical lead, comprising:

an outer insulation sidewall extending along a lead axis and having an outer diameter;

a coupling component formed from a slug of conductive material and being entirely contained within the outer diameter of the outer insulation sidewall, the coupling component including a crimping recess extending along one side of the component and a thickened portion offset laterally from the crimping recess and having a welding surface displaced laterally from the crimping recess, an electrode component mounted around the outer insulation sidewall, the electrode component including a first portion defining an electrode surface and a second portion extending from the first portion to within the outer diameter of the outer insulation sidewall and over the welding surface of the coupling component and being welded thereto, wherein the crimping recess comprises a crimp groove located between first and second arms extending laterally from the thickened portion, wherein the thickened portion comprises at least one groove therein in which the second portion of the electrode is located and wherein the at least one groove extends orthogonally with respect to the crimping.

\* \* \* \* \*